United States Patent
Srivastava et al.

(10) Patent No.: US 10,628,940 B2
(45) Date of Patent: Apr. 21, 2020

(54) AUTOMATED ANALYSIS OF ANGIOGRAPHIC IMAGES

(71) Applicant: THE CLEVELAND CLINIC FOUNDATION, Cleveland, OH (US)

(72) Inventors: Sunil K. Srivastava, Shaker Hts., OH (US); Justis P. Ehlers, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 187 days.

(21) Appl. No.: 14/847,772

(22) Filed: Sep. 8, 2015

(65) Prior Publication Data

US 2016/0071266 A1    Mar. 10, 2016

Related U.S. Application Data

(60) Provisional application No. 62/047,249, filed on Sep. 8, 2014, provisional application No. 62/052,186, filed on Sep. 18, 2014.

(51) Int. Cl.
| | | |
|---|---|---|
| G06K 9/00 | (2006.01) | |
| G06T 7/00 | (2017.01) | |
| G06T 11/00 | (2006.01) | |
| A61B 3/14 | (2006.01) | |
| G06T 7/33 | (2017.01) | |

(Continued)

(52) U.S. Cl.
CPC ............ *G06T 7/0012* (2013.01); *A61B 3/145* (2013.01); *G06T 7/0016* (2013.01); *G06T 7/11* (2017.01);
(Continued)

(58) Field of Classification Search
CPC ....... G06T 7/0012; G06T 7/187; G06T 7/254; G06T 7/11; G06T 7/30; G06T 7/33;
(Continued)

(56) References Cited

U.S. PATENT DOCUMENTS 7,668,351 B1 *  2/2010  Soliz ..................... G06T 7/155
                                                351/237
8,098,907 B2 *  1/2012  Yan ....................... G06T 7/0012
                                                382/128

(Continued)

FOREIGN PATENT DOCUMENTS

| DE | 10317367 A1 | 11/2004 |
| EP | 1081647 A1 | 7/2001 |
| WO | 03030073 A1 | 4/2003 |

OTHER PUBLICATIONS

Dubow, Michael, et al. "Classification of Human Retinal Microaneurysms Using Adaptive Optics Scanning Light Ophthalmoscope Fluorescein AngiographyClassification of Retinal Microaneurysms." Investigative ophthalmology & visual science 55.3 (2014): 1299-1309.*

(Continued)

*Primary Examiner* — Jonathan S Lee
(74) *Attorney, Agent, or Firm* — Tarolli, Sundheim, Covell & Tummino LLP

(57) ABSTRACT

Systems and methods are provided for automated analysis of angiographic images. An angiographic imaging system is configured to capture a first image of a region of interest, representing a first time, and a second image of a region of interest, representing a second time. A registration component is configured to register the first image to the second image. A difference component is configured to generate a difference image from the first image and the second image. A pattern recognition component is configured to assign a clinical parameter to the region of interest from the difference image and at least one of the first image and the second image.

13 Claims, 3 Drawing Sheets

(51) Int. Cl.
*G06T 7/11* (2017.01)
*G06T 7/30* (2017.01)
*G06T 7/187* (2017.01)
*G06T 7/254* (2017.01)

(52) U.S. Cl.
CPC .............. *G06T 7/187* (2017.01); *G06T 7/254* (2017.01); *G06T 7/30* (2017.01); *G06T 7/33* (2017.01); *G06T 11/003* (2013.01); *G06T 2207/10016* (2013.01); *G06T 2207/20084* (2013.01); *G06T 2207/30041* (2013.01); *G06T 2207/30101* (2013.01); *G06T 2207/30104* (2013.01); *G06T 2211/404* (2013.01)

(58) Field of Classification Search
CPC ......... G06T 7/0016; G06T 2207/10016; G06T 2207/20084; G06T 2207/30041; G06T 2207/30101; G06T 2207/30104; A61B 3/145
USPC ....................................................... 382/130
See application file for complete search history.

(56) References Cited

U.S. PATENT DOCUMENTS

| | | | | |
|---|---|---|---|---|
| 8,879,813 | B1 * | 11/2014 | Solanki ................ | G16H 30/20 382/128 |
| 8,896,682 | B2 * | 11/2014 | Bressler ............... | A61B 3/0025 348/78 |
| 9,002,085 | B1 * | 4/2015 | Solanki ................ | G06T 7/0014 382/128 |
| 9,538,925 | B2 * | 1/2017 | Sharma et al. | |
| 10,010,255 | B2 * | 7/2018 | Fonte et al. | |
| 2015/0029464 | A1 * | 1/2015 | Jayasundera ......... | G06T 7/0016 351/246 |

OTHER PUBLICATIONS

Berger, Jeffrey W., and Jonathan Yoken. "Computer-assisted quantitation of choroidal neovascularization for clinical trials." Investigative ophthalmology & visual science 41.8 (2000): 2286-2295.*

Manivannan, Ayyakkannu, et al. "Ultra-wide-field fluorescein angiography of the ocular fundus." American journal of ophthalmology 140.3 (2005): 525-527.*

Campbell, John Peter, et al. "Wide-field retinal imaging in the management of noninfectious posterior uveitis." American journal of ophthalmology 154.5 (2012): 908-911.

Kempen, John H., et al. "Fluorescein angiography versus optical coherence tomography for diagnosis of uveitic macular edema." Ophthalmology 120.9 (2013): 1852-1859.

Nicholson, Benjamin P., et al. "Comparison of wide-field fluorescein angiography and 9-field montage angiography in uveitis." American journal of ophthalmology 157.3 (2014): 673-677.

Patel, Ravi D., et al. "Characterization of ischemic index using ultra-widefield fluorescein angiography in patients with focal and diffuse recalcitrant diabetic macular edema." American journal of ophthalmology 155.6 (2013): 1038-1044.

Sim, Dawn A., et al. "Patterns of peripheral retinal and central macula ischemia in diabetic retinopathy as evaluated by ultra-widefield fluorescein angiography." American journal of ophthalmology 158.1 (2014): 144-153.

Singer, Michael, et al. "Area of peripheral retinal nonperfusion and treatment response in branch and central retinal vein occlusion." Retina 34.9 (2014): 1736-1742.

Wessel, Matthew M., et al. "Peripheral retinal ischaemia, as evaluated by ultra-widefield fluorescein angiography, is associated with diabetic macular oedema." British Journal of Ophthalmology (2012): bjophthalmol-2011.

Kang, Dong-Goo, Dae Chul Suh, and Jong Beom Ra. "Three-dimensional blood vessel quantification via centerline deformation." Medical Imaging, IEEE Transactions on 28.3 (2009): 405-414.

Patton, Niall, et al. "Retinal image analysis: concepts, applications and potential." Progress in retinal and eye research 25.1 (2006): 99-127.

International Search Report and Written Opinion for PCT/US2015/048929, dated Dec. 23, 2015, pp. 1-13.

* cited by examiner

AUTOMATED ANALYSIS OF ANGIOGRAPHIC IMAGES

RELATED APPLICATIONS

This application claims priority to each of U.S. Provisional Patent Application Ser. No. 62/047,249, filed Sep. 8, 2014 and U.S. Provisional Patent Application Ser. No. 62/052,186, filed Sep. 18, 2014. Each of these applications is hereby incorporated by reference.

TECHNICAL FIELD

The present invention relates generally to medical imaging systems, and more particularly to automated analysis of angiographic images.

BACKGROUND OF THE INVENTION

Retinal vascular disease represents a collection of diseases that are among the most frequent causes of blindness. Diabetic retinopathy and retinal vascular occlusive diseases represent the most common of these disorders. Common angiographic features in these conditions include vascular staining/leakage, microaneurysms, capillary nonperfuslon, and neovascularization. Significant recent advances have occurred in the therapeutic options for these conditions including pharmacologies (e.g., steroids, anti-VEGF) and laser (e.g., panretinal photocoagulation, micropulse, focal laser).

SUMMARY OF THE INVENTION

In accordance with an aspect of the present invention, an imaging system includes an angiographic imaging system configured to capture a first image of a region of interest, representing a first time, and a second image of a region of interest, representing a second time. A registration component is configured to register the first image to the second image. A difference component is configured to generate a difference image from the first image and the second image. A pattern recognition component is configured to assign a clinical parameter to the region of interest from the difference image and at least one of the first image and the second image.

In accordance with another aspect of the present invention, a method is provided for evaluating a region of interest of a patient. A first image of a region of interest, representing a first time, is captured. A second image of the region of interest, representing a second time, is captured. The first image is registered to the second image. A difference image is generated from the first image and the second image. Until a termination event occurs, a next subregion within one of the difference image, the first image, and the second image is selected and a rule-based classification is applied to the selected subregion to assign a clinical parameter to the subregion.

In accordance with yet another aspect of the present invention, a method is provided method for evaluating a region of interest of a patient. A first image of a region of interest, representing a first time, is captured. A second image of the region of interest, representing a second time, is captured. The first image is registered to the second image. A difference image is generated from the first image and the second image. A plurality of features are extracted from the difference image and at least one of the first image and the second image. A clinical parameter is assigned to the region of interest according to the extracted features.

DETAILED DESCRIPTION OF INVENTION

Uveitis represents a collection of inflammatory diseases which affect the eyes. Inflammation within the eye can lead to changes in retinal and choroidal vascular flow. More commonly, inflammation leads to changes in the blood vessels which allow the angiographic dye to leak out of the vessels. In those with severe disease, the amount of leakage that occurs is greater than those with mild or quiet disease.

Objective and quantitative assessment of angiographic imaging is currently lacking. Previously, the only way to assess the amount of vascular leakage was either to manually measure the area of leakage on standard view angiograms in millimeters squared or to assess qualitatively the type of leakage (diffuse. petalloid, focal). Subjective interpretation of angiographic patterns and features limit the analysis and potential of utilizing the modality as a true biomarker of diagnostic and therapeutic value. The inventors have determined that the complex patterns noted within angiography, including staining, leakage, pooling, blockage, nonperfusion, and window defects are amenable to quantitative assessment and integrative analysis for pattern recognition. Specifically, this complex pattern analysis can be utilized to create an activity fingerprint with value in therapeutic assessment and monitoring.

The systems and methods herein provide in-depth analysis of the amount and type of leakage in the form of pixels per area of the retina or choroid using an objective computerized assessment tool. Assessment is performed at various time points during the angiogram to allow for normalization to assess not only baseline abnormalities in fluorescence, but to also enable assessment of change over lime to facilitate identification and quantification of leakage. Longitudinal assessment is also able to be performed over time to assess treatment response, change in disease activity, and overall disease burden.

Figure 1:
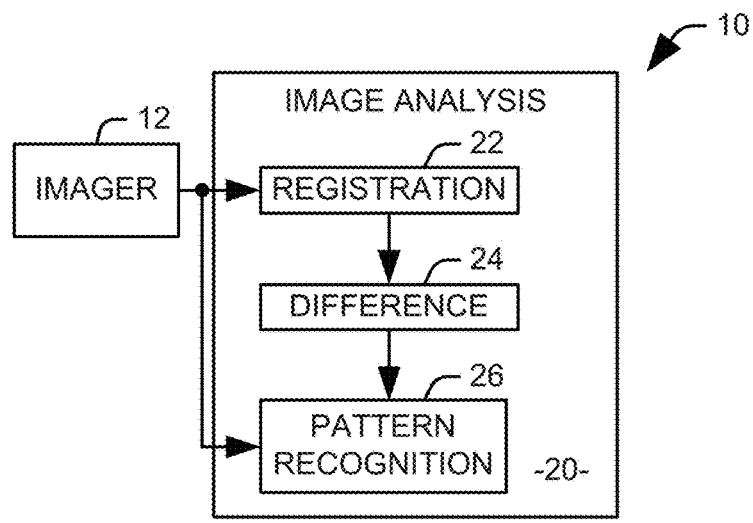
FIG. 1 illustrates an imaging system in accordance with an aspect of the present invention.

FIG. 1 illustrates an imaging system 10 in accordance with an aspect of the present invention. The imaging system 10 includes an imager 12 configured to capture images of a region of interest to provide an angiogram. It will be appreciated that the imager 12 will generally be employed in concert with a contrast dye to allow for ready identification of blood vessels within the region of interest. In one implementation, the region of interest is within an eye of a patient or subject and the imager operates within either the visible or infrared light bands to produce ultra wideband angiographic images of the retinal and choroidal vessels with 180-200 degrees of view to provide a panretinal view of the vessels. In this implementation, examples of contrast dyes can be fluorescein and indocynanine.

First and second images of the region of interest, representing the region of interest at respective first and second times, can be captured at the imager 12 and provided to an image analysis system 20 to identify disorders associated with blood flow within the image. In one example, the image analysis system 20 evaluates the images to identify vessel leakage, microaneurysms, ischemia, and neovascularization. The image analysis system 20 includes a registration component 22 that registers one of the first and second images to the other of the first and second images. A difference component 24 creates a difference image from the registered images. It will be appreciated that the resulting difference image can represent a simple subtraction of pixel values from the raw images or involve a degree of image conditioning to either or both of the first and second images and/or the resulting difference image. For example, the difference image can be filtered to remove background noise before analysis.

At least one of the first and second images and the difference image are then provided to a pattern recognition component 26. The pattern recognition component 26 is configured to evaluate the difference image and either or both of the first and second images to assign a clinical parameter to the imaged region of interest. In one implementation, the pattern recognition component 26 can utilize a rule-based classification process to identify localized disorders in subregions within the imaged region. For example, diffuse bright regions within the difference image can represent vessel leakage between the capture of the first and second images, defined bright regions within the difference image can represent neovascularization, areas of brightness adjacent to a vessel within the first or second image can represent a microaneurysm, and regions of diminished brightness within the first and second images can represent ischemia. To detect these regions, the pattern recognition component 26 can use a windowing approach in which one or more regions of the image are analyzed individually according to stored rule sets.

Alternatively or additionally, a plurality of global features can be extracted from the first and second images and the difference image and provided to the pattern recognition component 26 to select an appropriate clinical class according to the extracted features. It will be appreciated that a clinical parameter, as used herein, can be a categorical parameter, representing a specific disorder or a clinical treatment that is likely to be useful for the region of interest, or a continuous parameter, such as a metric representing a likelihood that a given treatment will be successful, a likelihood that a particular disorder is present, or an index indicating the prevalence of various localized disorders. In one implementation, the number and/or locations of localized disorders can be used as features in subsequent assignment of a clinical parameter.

In one implementation, the pattern recognition component 26 can comprise one or more pattern recognition classifiers, each of which utilize the extracted features or a subset of the extracted features to determine an appropriate clinical parameter for the occupant. Where multiple classifiers are used, an arbitration element can be utilized to provide a coherent result from the plurality of classifiers. Each classifier is trained on a plurality of training images representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, ensemble methods, rule based systems, or artificial neural networks. In one implementation, the outcome class can represent a predicted range of outcomes for the patient given the application of the therapeutic procedure. This can range from a binary "good" and "bad" to a plurality of graduations of expected success. From the provided feature vector, an outcome class is selected and a confidence in the selected result can be calculated. Results falling below a threshold confidence value can be rejected.

For example, a support vector machine (SVM) classifier can process the training data to produce functions representing boundaries in a feature space defined by the various attributes of interest. Similarly, an artificial neural network (ANN) classifier can process the training data to determine a set of interconnection weights corresponding to the interconnections between nodes in its associated the neural network.

A SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. A rule-based classifier applies a set of logical rules to the extracted features to select an output class. Generally, the rules are applied in order, with the logical result at each step influencing the analysis at later steps.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

In another implementation, the pattern recognition component 26 can include a regression model configured to provide calculate a parameter representing a likelihood that the patient has a given disorder, a likelihood that a patient will respond to a specific therapeutic procedure, or an extent to which a patient is affected by a given disorder. In yet another implementation, the pattern recognition component 26 can perform a sensitivity analysis using the model, such that a magnitude of the effect of one or more features on the at least one parameter can be determined.

The system 10 allows quantification of vascular leakage which would allow a more precise evaluation of retinal or choroidal vascular flow. The ability to quantify amount of leakage would allow assessment on level of activity of inflammation, provide a durable outcome measure for clinicians to follow and to titrate therapy, and provide a reproducible outcome measure for clinical trials and drug development. There is no accepted measure for wide angle angiographic leakage in uveitis patients, and the lack of durable outcome measures in uveitis slows the development of novel therapies. As uveitis has rare disease classification from the FDA, there is great interest within the pharmaceutical industry to develop novel therapies. However, as the outcomes measures are poorly reproducible, there is a need for the robust, reproducible measures of ocular inflammation provided by the system 10.

Figure 2:
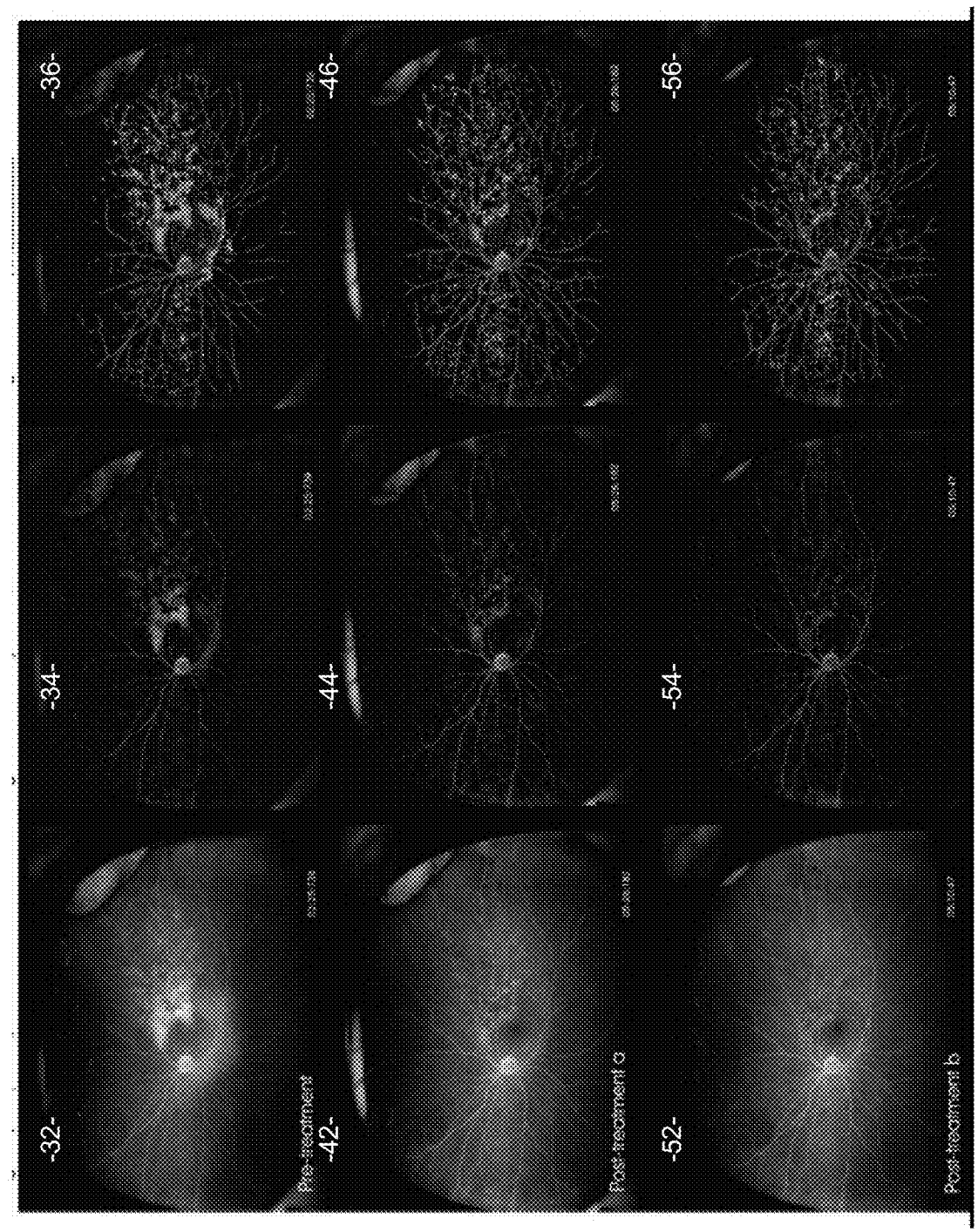
FIG. 2 illustrates one example of quantifying a treatment outcome, specifically a degree of inflammation, using the system of FIG. 1.

FIG. 2 illustrates one example of quantifying a treatment outcome, specifically a degree of inflammation, using the system of FIG. 1. The first column of images 32, 34, and 36 are raw images of the eye. These are the most recent, or "late phase" images, or in the language of FIG. 1, the second image. In the second column of images 42, 44, and 46, the late phase image has been registered to a previous "early phase" image and normalized to reduce noise. The third column of images 52, 54, and 56 illustrate the image after an automated search for local disorders. In the illustrated image, patches of solid gray are leakage from the vessels, indicating inflammation in those regions.

The first row of images 32, 42, and 52 represent the eye before treatment. It can be seen from the analyzed image 52 that a large amount of inflammation is present. Each of the second row of images 34, 44, and 54 and the third row of images 36, 46, and 56 represent the eye after a first treatment and a second treatment, respectively, have been applied. It will be appreciated from the analyzed images 54 and 56 that the amount of inflammation in the eye has been significantly reduced. The automated location of inflammation allows for the response to the treatment to be quantified, making it possible to reliably determine the effectiveness of the treatment.

Figure 3:
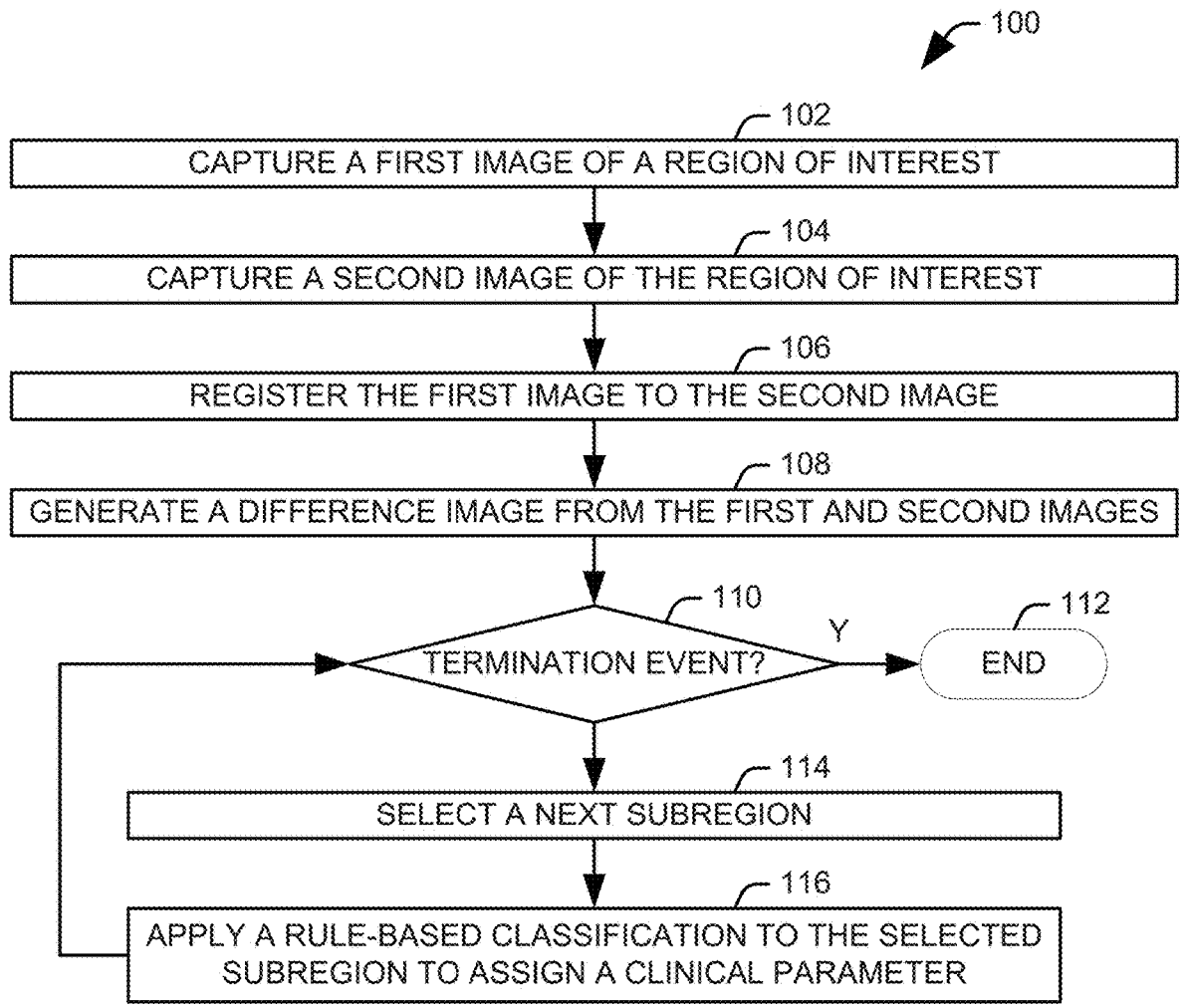
FIG. 3 illustrates a method for evaluating a region of interest of a patient.
Figure 4:
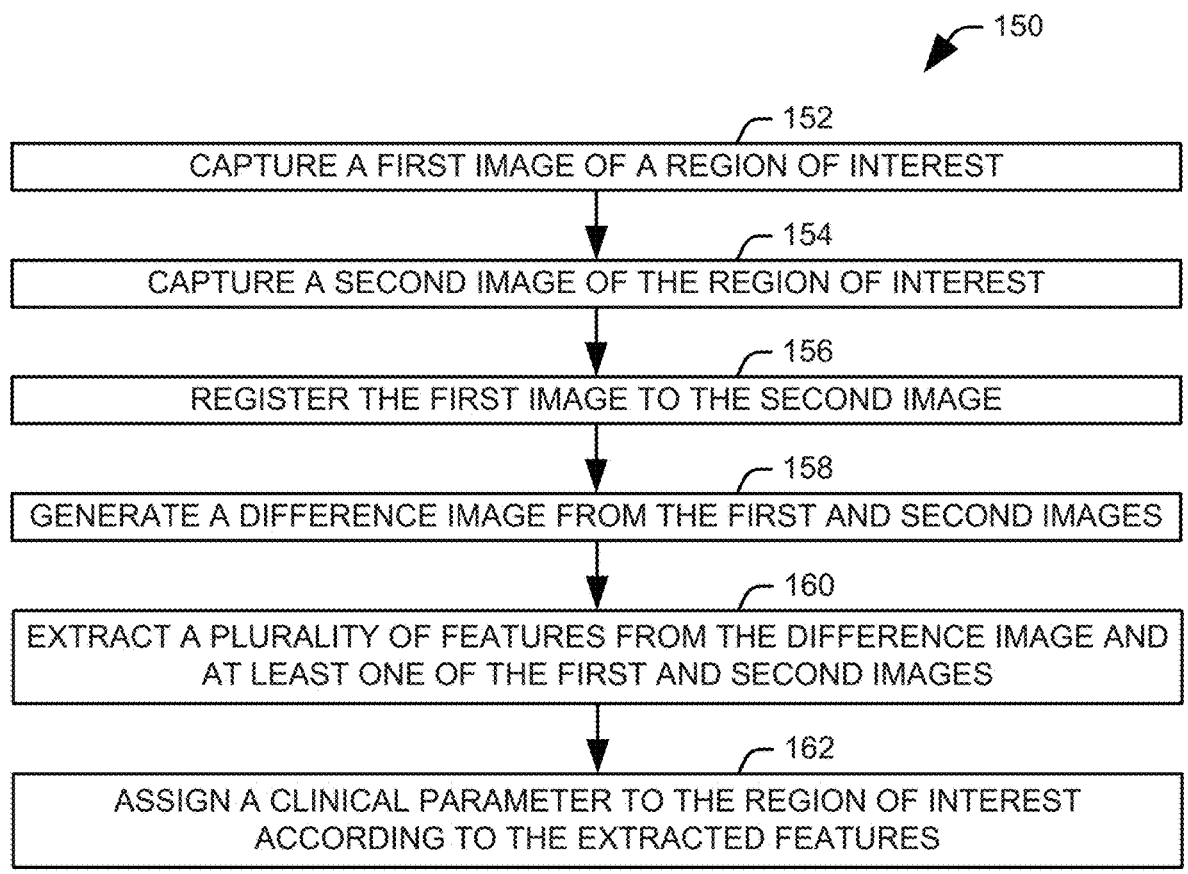
FIG. 4 illustrates another method for evaluating a region of interest of a patient.

In view of the foregoing structural and functional features described above, a methodology in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 3 illustrates a method 100 for evaluating a region of interest of a patient. At 102, a first image of a region of interest, representing a first time, is captured. At 104, a second image of a region of interest, representing a second time, is captured. In one implementation, each of the first and second images are captured as an ultra wide field view of the retinal and choroidal vessels of an eye of the patient. In this implementation, the imaging can include administering a contrast to the patient, such as fluorescein and indocynanine green. At 106, the first image is registered to the second image. At 108, a difference image is generated from the first image and the second image. In one example, the difference image is formed as a direct pixel-by-pixel subtraction of the registered images. In another example, noise filtering is applied to the resulting subtraction to account for differences in the background noise within the two images.

At 110, it is determined if a termination event has occurred. A termination event can include the evaluation of all of a plurality of subregions within the region of interest, evaluation of a predetermined set of subregions, or the passage of a predetermined amount of time. If so (Y), the method terminates at 112. If not (N), a next subregion is selected within one of the difference image, the first image, and the second image at 114. At 116, a rule-based classification is applied to the selected subregion to assign a clinical parameter to the subregion. In one implementation, a global clinical parameter to region of interest according to the clinical parameters assigned to the plurality of subregions. For example, the global clinical parameter can represent a total area or percentage of the imaged area affected by a given disorder.

In one implementation, the assigned clinical parameter is categorical, with available categories for each subregion including one of ischemia, neovascularization, microaneurysms, vessel leakage, and normal. In one implementation, subregions can be evaluated in each image to allow for different disorders to be detected. To this end, when a subregion is selected in the difference image, the rule-based classification can assign the clinical parameter by categorizing each subregion as normal, neovascularization, or vessel leakage. When a subregion is selected in either the first image and the second image, the rule-based classification can assign the clinical parameter by categorizing each subregion as normal, microaneurysm, or ischemia. In this instance, the subregion can retain multiple classifications, or an arbitration can be applied to provide a final category for each subregion.

FIG. 4 illustrates another method 150 for evaluating a region of interest of a patient. At 152, a first image of a region of interest, representing a first time, is captured. At 154, a second image of a region of interest, representing a second time, is captured. In one implementation, each of the first and second images are captured as an ultra wide field view of the retinal and choroidal vessels of an eye of the patient. In this implementation, the imaging can include administering a contrast to the patient, such as fluorescein and indocynanine green. At 156, the first image is registered to the second image. At 158, a difference image is generated from the first image and the second image. In one example, the difference image is formed as a direct pixel-by-pixel subtraction of the registered images. In another example, noise filtering is applied to the resulting subtraction to account for differences in the background noise within the two images.

At 160, a plurality of features are extracted from the difference image and at least one of the first image and the second image. In one implementation, descriptive statistics can be determined for the brightness values of various anatomical regions of the eye. To this end, one or more of the images can be registered to a generic atlas of the eye, and appropriate statistics, such as average values (mean, median, etc.) and deviation values (variance, range, etc.), can be calculated for each region. Alternatively or additionally, clinical parameters can be assigned to subregions within the region of interest, as described in FIG. 3, and the assigned parameters can be used as features. At 162, a clinical parameter is assigned to the region of interest according to the extracted features. In the illustrated implementation, the clinical parameter can represent, for example, a best treatment for the patient, a disorder likely associated with the region of interest, a likelihood that a specific treatment will be successful, and a likelihood that a given disorder is present.

Figure 5:
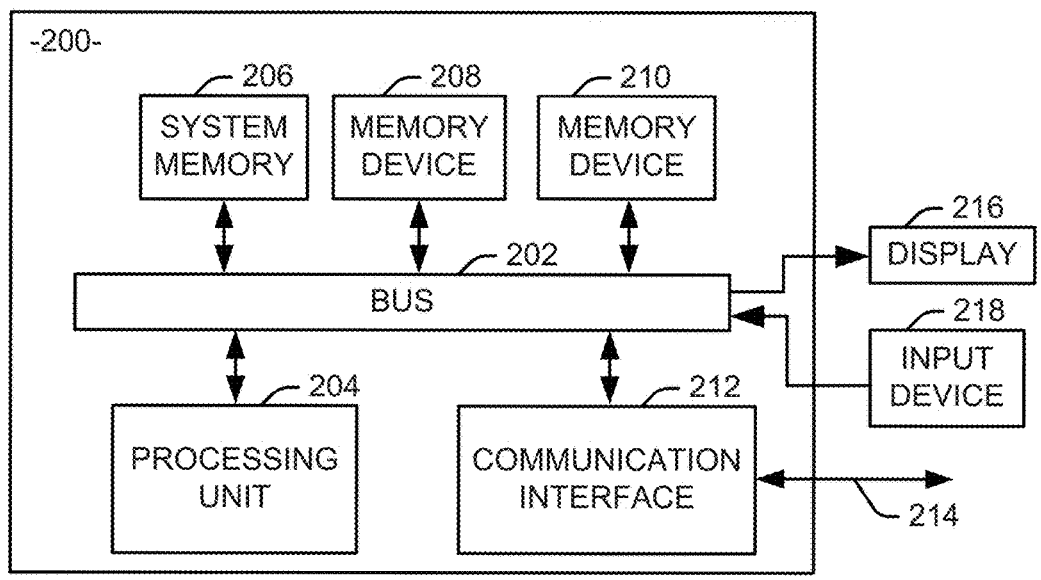
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 200 of hardware components capable of implementing examples of the systems and methods disclosed in FIGS. 1-4, such as the image analysis component 20 of FIG. 1. The system 200 can include various systems and subsystems. The system 200 can be a personal computer, a laptop computer, a workstation, a computer system, an appliance, a "smart" phone, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings. Additionally or alternatively, the system 200 can access an external data source or query source through the communication interface 212, which can communicate with the system bus 202 and the communication link 214.

In operation, the system 200 can be used to implement one or more parts of an angiograph imagings system. Computer executable logic for implementing the image analysis component 20 resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can include either a single medium or multiple non-transitory media operatively connected to the processing unit 204.

What has been described above includes exemplary implementations of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Having described the invention, the following is claimed:

1. An imaging system comprising:
   an angiographic imaging system configured to capture a first image of a region of interest, representing a first time, and a second image of a region of interest, representing a second time;
   a processor; and
   a non-transitory computer readable medium storing machine readable instructions executable by the processor to provide:
      a registration component configured to register the first image to the second image;
      a difference component configured to generate a difference image from the first image and the second image; and
      a first pattern recognition component configured to assign a first clinical parameter to the region of interest from one of the first image and the second image;
      a second pattern recognition component configured to assign a second clinical parameter to the region of interest from the difference image; and
      an arbitration component configured to select a third clinical parameter for the region of interest from the first clinical parameter and the second clinical parameter.

2. The imaging system of claim 1, the second pattern recognition component being configured to assign a clinical parameter to each of a plurality of subregions within the region of interest.

3. The imaging system of claim 2, the second pattern recognition component being configured to utilize a windowing approach in which each subregion of the image is analyzed individually according to at least one stored rule set to assign a clinical parameter to the subregion.

4. The imaging system of claim 2, wherein the pattern recognition component is configured to identify microaneurysms.

5. The imaging system of claim 1, wherein the second pattern recognition component is configured to identify a first of ischemia, neovascularization, microaneurysms, and vessel leakage from the difference image and the first pattern recognition component is configured to identify a second of ischemia, neovascularization, microaneurysms, and vessel leakage from the at least one of the first image and the second image.

6. The imaging system of claim 2, wherein the second pattern recognition component is configured to assign a global clinical parameter to the region of interest according to at least the clinical parameters assigned to the plurality of subregions.

7. The imaging system of claim 1, the third clinical parameter representing the presence or absence of a disorder within the region of interest.

8. The imaging system of claim 1, the third clinical parameter representing a likelihood that a specific treatment will be successful.

9. The imaging system of claim 1, the third clinical parameter representing a likelihood that a specific disorder is present in the region of interest.

10. A method for evaluating a region of interest of a patient comprising:
   capturing a first image of a region of interest, representing a first time, as an ultra wideband angiographic image;
   capturing a second image of the region of interest, representing a second time, as an ultra wideband angiographic image;

registering the first image to the second image;

generating a difference image from the first image and the second image;

assigning a first clinical parameter to the region of interest from one of the first image and the second image;

assigning a second clinical parameter to the region of interest from the difference image; and assigning a third clinical parameter to the region of interest according to the first clinical parameter and the second clinical parameter.

11. The method of claim 10, wherein each of capturing the first image of the region of interest and capturing the second image of the region of interest comprises capturing an ultra wide field view of the retinal and choroidal vessels of an eye of the patient.

12. The method of claim 10, the second clinical parameter representing a percentage of the imaged region affected by a disorder.

13. The method of claim 10, wherein each of capturing the first image of the region of interest and capturing the second image of the region of interest comprises administering one of fluorescein and indocyanine green contrast to the patient.

* * * * *